United States Patent [19]

Davis

[11] Patent Number: 5,158,772

[45] Date of Patent: Oct. 27, 1992

[54] UNIQUE BACTERIAL POLYSACCHARIDE POLYMER GEL IN COSMETICS, PHARMACEUTICALS AND FOODS

[76] Inventor: Walter B. Davis, 1321 Wakarusa Dr., Lawrence, Kans. 66049

[21] Appl. No.: 763,987

[22] Filed: Sep. 23, 1991

[51] Int. Cl.$^5$ .......................... A61K 9/70; A61K 9/06; A61K 47/36
[52] U.S. Cl. .................................... 424/401; 424/439; 424/443; 424/479; 424/49; 424/DIG. 13; 536/4.4; 435/74; 435/850
[58] Field of Search .......................................... 424/401

[56] References Cited

U.S. PATENT DOCUMENTS 4,908,310  3/1990  Buller ................................. 435/101
4,941,533  7/1990  Buller et al. ........................ 166/252

Primary Examiner—Thurman K. Page
Assistant Examiner—Raj Bawa
Attorney, Agent, or Firm—Zarley, McKee, Thomte, Voorhees, & Sease

[57] ABSTRACT

Topical compositions for application to the skin comprising a topically active agent which may be a cosmetic agent or a therapeutic agent, and a small, but carrier effective amount of a microbial polysaccharide polymer gel which is a beta-1,3 glucan-type polysaccharide.

6 Claims, No Drawings

UNIQUE BACTERIAL POLYSACCHARIDE POLYMER GEL IN COSMETICS, PHARMACEUTICALS AND FOODS

BACKGROUND OF THE INVENTION

This invention relates primarily to cosmetic, pharmaceutical and secondarily to food additive composition products and to the formulation of such products. Some of the products which can be prepared by skilled cosmetic and pharmaceutical chemical formulators based upon the polymer gel of this invention include suntan lotions, facial lotions, hand lotions, body lotions, topical prescription treatment lotions and creams.

One can also use the basic topical composition containing the microbial polysaccharide polymer gel of this invention for preparation of therapeutic compositions, and for other topical applications such as ointments, creams, and occlusive dressings, and also to help transport medicaments through the skin.

Products which are either oil-in-water emulsions or water-in-oil emulsions are in many instances not cosmetically attractive to consumer users. Often a negative reaction caused by the lack of desirable skin feel makes the consumer conclude that the product is ineffective, or the product may lack aesthetics. Suspensions and flocs of solid phases and 3-phase systems are also incorporated in the present invention.

All-oil topical lotions likewise have significant deficiencies in that, in many instances, the consumer does not regard such products as "cosmetically elegant". "Cosmetically elegant" is a term used in the cosmetic formulation art to describe a product which is attractive appearing, has good skin feel, is non-greasy, not tacky, spreadable, and soft. All of these terms generally relate to the consumer user's rating of the product in terms of its attractiveness and skin feel. All-oil products are often regarded as not cosmetically elegant in that they tend to have an excessively greasy feel, and often may soil clothing or other items coming into contact with them.

Likewise, water-soluble products have certain deficiencies. The primary deficiency of such products is short treating life on the skin since they are easily washed off. Then too, many water-based products are often described by the consumer user as lacking cosmetic elegance. They lack good skin feel, giving an overall impression of wetness, and lack of substantiavity, with the consumer paying for a product often containing over 75% water, which by itself has only transient therapeutic value for the skin.

It therefore can be seen that topical products as prepared by cosmetic and pharmaceutical chemical formulators, generally involve a balancing and trade off, of the good and bad points of the four basic types of topicals: namely oil-in-water emulsions; water-in-oil emulsions; oleaginous lotions; or, all-water soluble lotions. Ointments, creams, semi-solid bases and suspensions similarly can suffer drawbacks. While each has certain advantages, each also has significant disadvantages. It is for the reason of this balancing and trade off of properties that most formulators, for the most part, have abandoned all-oil and all-water soluble products and have adopted topical preparations which are either oil-in-water emulsions or water-in-oil emulsions.

The fundamental object in preparing such products is to prepare something which is a good emollient, physiologically compatible, a good skin moisturizer, a product which is cosmetically elegant, and a product which has the added benefit of the base topical composition providing for increased and/or prolonged activity of any added active ingredient, such as steroids, humectants, moisturizes, pharmaceuticals, or the like.

One fundamentally important criteria against which many such topical lotions, especially cosmetic ones, must be measured is their ability to act as efficient skin moisturizers. Skin moisturizing ability is of extreme importance for topical cosmetics in that consumers regard flaky, dry skin as unsightly and undesirable. Thus, products which are topical and have the added benefit of enhancing skin moisture retention capabilities, have a significant added benefit above and beyond the utility of their active ingredient, whether a cosmetic, a medicament, or the like.

Much has been written on the causative factors for dry, flaky and scaly skin. As those skilled in cosmetic formulation theorize, when one speaks of dry and flaky skin, one is speaking of the loss of water from the stratum corneum, which is the outermost dead layer of skin. It is believed that whenever moisture is removed from the stratum corneum, it loses its soft suppleness and becomes dry and scaly.

Some dermatologists believe that dryness is due to a loss of the water-binding fatty materials from the stratum corneum layer, while others state that "dry" skin really does not lack water. Most, however, seem to agree that four basic stages are involved in the development of dry skin. In the first stage, during cleansing, there is removal of the sebum that protects water binding materials in the stratum corneum against being leached out. In the second stage, there is, in fact, some loss of the water binding components of the stratum corneum. In the third stage after water evaporation and dehydration, there is a loss of flexibility of the stratum corneum cells. Finally, in the fourth stage, cracking of the stratum corneum occurs, allowing penetration of microorganisms and irritant materials into the epidermis. In extreme cases, infections, irritations, and rashes result.

The skin acts as a barrier to the ingress of liquids, chemicals and microorganisms which may otherwise penetrate to vital tissues. It also acts as a barrier to the loss of water from within. The barrier function is essentially in the very outermost layers of the skin known as the stratum corneum. Surprisingly, this essential barrier function is "delegated" to dead skin cells. These cells are formed at the basal layer of the skin and are soon committed to a programmed sequence of maturation, cell death and the formation of a constantly replenished layer of dead cells which are virtually insoluble in all but strong alkali, virtually impermeable to water and have a texture which is soft and malleable when moist, but hard and brittle when dry. In addition, low temperatures contribute to brittleness of the outer layers.

While it is not appropriate at this juncture to at length educate on the complexity of the skin, but the following highlights the essentials.

1. The barrier is comprised of flattened, dead, keratinized cells firmly attached by desmosomes and cemented together with multiple, ordered layers of lipid and water.
2. Loss of water is thought to be predominantly via the layers between the cells rather than across the dead cell membranes.

3. If the barrier function is disrupted, particularly by detergents or surfactant molecules, then the rate of water loss increases.
4. The water loss is by passive evaporation and is accelerated if the atmosphere has a low humidity.
5. A low humidity coupled with a low temperature can be particularly challenging to the integrity and water control function of the stratum corneum.
6. The water content of the skin is very difficult to measure, mainly because there is a steep concentration gradient within the outer layers and secondarily because any interference with the dynamic diffusion, evaporation and supply from below the surface will disrupt the water content of the portion of the skin being measured.
7. The water content of the skin has been measured indirectly, most successfully by the indirect process of measuring the electrical impedance of the skin. Despite a number of pedantic critics who mainly argue that the results are by inference only, the impedance techniques are very sensitive to water content changes in the outer layers of the epidermis and are reproducible. In the face of the fact that there is no satisfactory direct measurement technique, electrical impedance is the best route available to date. Our invention is known to change the electrical impedance in the same way as do other effective moisturizing enhancers/extenders.
8. Apart from the moisture content, the rate of transepidermal water loss (TEWL) is also of crucial importance and is not necessarily related to water content as referred to above. A high TEWL rate usually accompanies a high water content in the stratum corneum because the water activity is high and the lamellar lipid/water array is expanded thus mobilizing the diffusion of water from the inside to the outside where it evaporates. Note well, however, that a high TEWL rate means that the skin is losing a lot of water in a unit of time, therefore one might intuitively anticipate that the skin will become dry quickly. When moisturizers are applied, they often carry a large percent of product water with them which can replace the skin's natural source of water; however, unless the product increases the amount of water in the skin for a period longer than would pure water alone, it can hardly be described as a moisturizer in the sense that the advertisers of such products would have their customers believe. We suggest that a product is a moisturizer only if it increases the level of water in the skin for a period of time in excess of that achieved simply by wetting the surface with water.
9. The rate of TEWL is best measured without interfering with the water flux into the atmosphere. This is done admirably by a device well known to those skilled in the art of moisturizing the skin; i.e. the "Servomed" TEWL meter.
10. The topic of water balance and water flux in and through the skin is well documented in the literature, but some items of work are considerably better than others. See for example, to relevant work by M.D. Batt, et al., Journal of the Society of Cosmetic Chemists; W.A. Gerrard, Bioengineering and the Skin; and M.D. Batt and E. Fairhurst, International Journal of Cosmetic Science. These papers relate the consumer-detectable factors to the physico-chemical properties of moisturizer ingredients.

To date, the state of the art with regard to topicals involves reduction of water loss from the stratum corneum by two basic methods. In the first approach to the problem there is a deposit of an occlusive barrier layer to prevent water evaporation from the stratum corneum, the theory being that the deposit of, for example, petrolatum over the stratum corneum will act as a barrier to prevent excessive water loss outwardly therefrom. However, consumer users of such products often do not react favorably to such barrier creation because it is cosmetically inelegant, greasy, and often sticky. The second approach is to add hygroscopic substances to the stratum corneum in the hope that such substances will draw moisture which will penetrate into the stratum corneum, replacing lost moisture. It is upon this theory that compounds such as sodium lactate and sodium pyrolidone carboxylic acid are often added to topical lotions. Both sodium lactate and sodium pyrolidone carboxylic acid have been reported as naturally occurring in the stratum corneum. The use of such hygroscopic substances, however, does not cover the full range of requirements.

In summary, an effective topical composition must be an efficient moisturizer, long lasting, and preferably substantive, whatever else it is. An efficient moisturizer may be defined as a substance that overcomes the signs and symptoms of dry skin. This is interpreted by the consumer as providing a cosmetically elegant skin feel. As can be seen, there are deficiencies with many topical compositions, whether oil-in-water emulsions, water in oil emulsions, all-oil soluble phase, or all-water soluble phase. If the formulation contains high amounts of water there is a significant danger of bacterial growth and, if the product is an emulsion, there is danger of emulsion instability. Products containing large amounts of water easily wash off, and the water itself from the product only contributes transient efficacy.

Moreover, many of the topical products now on the market merely provide a physical barrier which is impervious to moisture, hoping that the skin will retain the moisture it has rather than providing a physiologically active agent for effective treatment of dry skin that is enduring. Moreover, in many instances in order to provide an enhanced degree of effective moisturization, there must be a corresponding sacrifice of cosmetic elegance.

In addition to cosmetic uses and cosmetic compositions, there is also a continuing need to provide excellent topical compositions for therapeutic uses such as topical medicaments and those which can be applied transdermally through the skin, topical medicament ointments, wound dressings, and the like. Such compositions can be prepared containing the microbial polymer gel composition and are suitable for both cosmetic and pharmaceutical uses and therapeutic compositions.

Accordingly, one object of the invention is to provide a topical composition which contains an effective amount of a microbial polysaccharide polymer which has the capability of enhancing/prolonging skin moisturization.

Another object of the invention is to provide a topical composition containing the microbial polymer gel of the present invention which allows the composition to maintain cosmetic elegance.

Still another object of the present invention is to provide a topical composition which is an excellent skin moisturizer.

Yet another object of the invention is to provide a topical composition useful for effective carrying of therapeutic and pharmaceutical agents so that they can be transported transdermally.

An even further object of the present invention is to provide a topical composition which is long lasting on the skin, which results in longer effective treating time for any active medicament which may be added thereto, and which can be used in a variety of compositions including cosmetic compositions, therapeutic compositions, wound dressings, topical steroid treatments, skin moisturizers, rubbing lotions, etc.

The formulations and methods by which the above objects as well as others may be accomplished as disclosed in the detailed description of the invention which follows hereinafter.

SUMMARY OF THE INVENTION

This invention relates primarily to a multi-purpose topical composition for application to skin. The composition is comprised of a topically active agent, whether a cosmetic agent or a therapeutic agent, and a small but effective amount of a microbial polysaccharide polymer which is a metabolic product of the gram positive microorganism, *Cellulomonas flavigena,* or the genetic equivalent thereof. Furthermore, the invention has unique power to modify the rheology of fluids and gels as applied to toiletries, pharmaceuticals, therapeutics, and food.

DETAILED DESCRIPTION OF THE INVENTION

Polymer gel material and its derivatives useful in the present invention is a water insoluble, microbial produced, polysaccharide polymer, resulting from aerobic cultivation of certain microorganisms known as *Cellulomonas flavigena.* Details of the organisms, the culturing of the organisms, and the isolation of the water-insoluble polysaccharide polymer gel are disclosed in the patent of Clarence S. Buller, U.S. Pat. No. 4,908,310 issued Mar. 13, 1990, the disclosure of which is fully incorporated herein as though set forth herein. The physical and chemical properties of the microbial beta 1-3 polyglucan important to this invention are the following:

Characteristics of the Microbial beta 1-3 Polyglucan:
Solubility:
1. Soluble in 0.1 N (or stronger) NaOH, concentrated formic acid and dimethyl sulfoxide.

2 Insoluble in water and organic solvents, but it gels.
Physical Properties:
1. Precipitates as a gel when alkaline solutions are neutralized.
2. Aqueous gel suspensions are not solubilized by heat.
3. The hydrogel is up to 97% water in composition.
4. Unaltered by repeated alkali-acid cycling.
5. Not degraded by heating at 121 degrees Celsius for at least 24 hours.
Chemical Properties:
1. The entire weight is accounted for as glucose units.
2. The polymer is a glucan homopolymer as indicated by thin layer and gas/liquid chromotography of $H_2SO_4$ hydrolysates.
3. The infra-red and nuclear magnetic resonance spectra show it is a member of the curdlan family, i.e. it is a linear polymer comprised of beta 1-3 glucosidic linkages.

4. It differs from known curdlans (produced by gram-negative bacteria in its degree of polymerization, D.P.) Known curdlans have D.P. in the range of 200–400, whereas the polymer described herein has a D.P. value near 550.

Without repeating the entire disclosure of the earlier patent, the polymer is synthesized by certain gram positive rod shaped bacteria which are cultured aerobically in a minimal salts medium containing a variety of carbohydrates and/or polysaccharides as carbon and energy sources. It is a glucan type polysaccharide polymer that is synthesized and apparently deposited externally as a capsule about the bacteria. In chemical composition, the polymer appears to resemble those beta 1-3 glucans which can be isolated from certain strains of *Streptococcus faecalis* subsp. myxogens in some species of agrobacterium (Harada, et al. 1968) and are known as curdlans but is apparently different in its gelation properties.

The polymer is produced by a bacterium that was isolated from decaying leaf litter. It was identified as *Cellulomonas flavigena* using standard bacteriological techniques. Microorganisms have been deposited at the American Type Culture Collection, Rockville, Maryland, and assigned the identification numbers ATCC 21399, ATCC 482, and ATCC 53703. In addition, another strain has been found which is suitable for the present invention and is herein identified as *Cellulomonas flavigena.* strain K.U. Strain K.U. has been deposited at ATCC and has ATCC deposit collection No. 53403. Any of these Cellulomonas flavigena organisms, or the genetic equivalent thereof are suitable for use in the present invention.

The term "genetic equivalent thereof" as used herein is intended to include the specific organisms, clones thereof, and organisms which are genetically altered but which contain the necessary genetic sequences from *Cellulomonas flavigena* to produce a desirable microbial polymer gel species suitable for use in the present invention.

The precise amounts of the polysaccharide polymer metabolic product, useful in a topical composition of the present invention will vary considerably depending upon the topical composition. However, for both cosmetic uses and for therapeutic uses typically the composition will contain from about 0.1% by weight to about 10% by weight, preferably from about 0.25% by weight to about 5% by weight of the polysaccharide gel.

While the bacteria known to produce the water-insoluble polysaccharide polymers are known as illustrated in the previous Buller Pat. No. 4,908,310, its use and advantageous use in topical compositions for cosmetics and topical therapeutic compositions has not heretofore been known suggested in the art. For example, Buller, et al., U.S. Pat. No. 4,941,533 issued July 17, 1990 teaches use of the microbial generated polysaccharides of U.S. Pat. No. 4,908,310 for subterranean permeability in a secondary oil recovery process. Other disclosure relating to uses of these unique polymer gels include those in a variety of publications of joint inventor Buller, namely:

Journal of Industrial Microbiology, 5 (1990) 125–130 R. Angelo, K.C. Voepel and C.S. Buller
Journal of Industrial Microbiology, 5 (1990) 131–138 K.D. Voepel and C.S. Buller
Journal of Industrial Microbiology, 5 (1990) 139–146 C.S. Buller and K.C. Voepel The basic ingredients of cosmetic compositions are well known to cosmetic formulators of ordinary skill in the art. For example, cosmetic lotions particularly are comprised of constituents such as propylene glycol and emollients such as isopropyl myristate and a preservative in addition to the active.

The exact composition will depend, as those of ordinary skill in the art of cosmetic formulation know, upon the ultimate purpose of use for the topical preparation. Some examples of suitable compositions which can be prepared utilizing the invention are suntan lotions, facial lotions, body lotions, topically applied steroid-containing lotions, hand lotions, medicated lotions, rubdown lotions, pre-shave lotions, and other topicals such as specialty preparations, hormone preparations, acid-/astringent preparations, lubricating creams, night creams and cream rouge.

As heretofore mentioned, the base topical composition of this invention may also be used as effective carriers for topical steroids. Thus, a corticosteroid such as the one sold under the trademark Topicort © by Hoechst-Roussel Pharmaceutical, Inc. of Somerville, N.J., may be employed with the lotions of this invention. Topicort, contains a corticosteroid known as desoximetasone and is used commonly at levels such as 0.25% in emollient creams and the like.

It is surprisingly discovered that the polymer produced by the gram positive microorganism (*Cellulomonas flavigena* strain K.U.) is remarkably compatible with and useful in a wide range of topical products. The K.U. strain produces this polymer (an insoluble polyglucan) by metabolism of carbohydrates such as starch-containing materials in aqueous solution. It is particularly useful for therapeutic and cosmetic products and for leave-on topical, therapeutic agents and topical products containing a drug or a pro-drug with local activity or systemic activity. Local activity is for this purpose defined as "treatment of the epidermis, dermis, hair, hair follicles, eccrine glands, endocrine glands, apocrine glands, and sebaceous glands." Systemic activity relates to drug or active molecules penetrating to the blood and/or lymph systems. The drug or pro-drug may penetrate via sweat ducts and hair follicles, sebaceous glands and/or via the classical transdermal route.

The polymer has the ability to control the fluidity and feel of topically applied products to great advantage. It has the ability to suspend solid and liquid phases in a manner akin to gums, gels, and products such as "Xanthan" and "Gantrez". It has a similar and in some ways superior group of properties and uses, to cellulose derivatives such as carboxy methyl cellulose and related cellulose derivatives.

The polymer has the main advantage of controlling the supply and loss of water from its unique gel network to and from the stratum corneum in a unique way. It holds up to 33 time its weight of water and allows a skin care and cosmetics formulator to carry water to the skin and hold it there. It is an aesthetically pleasing composition which also controls the release of the water for "use" by the dry skin. This property is especially useful for dry skin as in cases of aged, damaged, sun-damaged, or abused skin.

The slight tendency to form a film is an added advantage of the aqueous polymer combination in that the high water content gel may be applied to dry or susceptible skin surfaces before, during, or after exposure to environmental attack. The controlled release of the water, combined in this pleasant-feeling gel is particularly useful for decorative cosmetic and therapeutic skin-care formulators.

In addition to the supply and control of water in this convenient, pleasant polymer compound is the bonus factor in controlling the viscosity, thixotropy and tackiness of cream, ointments, lotion, tonic products, and foods. While its main therapeutic benefits can usually be achieved in leave-on products the benefits in product feel, viscosity control, etc. will not be lost to experienced formulators who are aware of the importance of the feel and appearance and handling characteristics of aqueous, wash-off formulations.

In addition to the obvious chemical, physical and physiological benefits of this polymer there are three other attributes of great importance. Firstly, it is a wholly natural product, manufactured from natural products, some of which could otherwise contribute to ecological waste pressures if not utilized to produce this polymer. Secondly, it is the extra-cellular exudate of gram-positive bacteria which means that it is unlikely to contain any endotoxins even in its unprocessed state. This in turn means that it will have widespread uses in products which come in intimate contact with the skin, mucosa, or indeed when ingested even when exposure is long-term. Thirdly, the polymer is amenable to the formation of derivatives which have modified physical and chemical properties. For instance, the hydrophilic:-lipophilic (HLB) ratio can be altered.

With regard to therapeutic uses, which involve enhancement of transdermal drug delivery, this invention relies primarily but not exclusively on the control of water in the epidermis. With respect to the polymers dermal hydration control microbial polymer gel has the added advantage of being compatible with and augmenting other humectants such as glycerol, propylene glycol, and water. In addition, it was discovered that certain alcohols in combination with the polymer enhanced transdermal drug delivery together with or in the absence of surface active agents. The surfactant agents are known to enhance drug and prodrug transdermal penetration by disrupting the skin barrier function thus interfering with the water/lipid, organized array. Without precisely wishing to be bound by any theory, it is possible that the water and alcohol referred to works by adding to the water content of the stratum corneum, thereby reducing the barrier function by virtue of increased water content alone.

It is believed that because of the ability of the polymer to bind many times its weight of water that it results in controlled release of the water to the skin in a remarkably pleasant-feeling topical formulation. The polymer is a natural product, it is safe to use beyond question and its ease of purification as described in the prior patents known and easily accomplished.

While applicants have not yet used this unique polymer gel in the many fields of potential applications that are possible, the current uses so far would at least suggest possibilities that it may be used in the following cosmetic, pharmaceutical, and food applications:

1. where normal thickening and gelling agents are used in the food industry, manufacture of cosmetics, and powder handling. Where water affinity without tackiness is valuable, this polymer can replace other gums, thickeners, binding agents and suspending agents;
2. in the powder form to stabilize dry powders;
3. slow release of a dye, disinfectant, or similar active can be facilitated by adding to an aqueous system, such as a water tank, a slow-dissolving alkali either connected to, or separately from the gelled active agent;
4. because of the chemical inertness of this polymer it is useful for use in surfactants where other "thickeners" may be incompatible;
5. use as a thickener, hair conditioner, and foam stabilizer in shampoos and other cosmetics and topical products;
6. because it is a natural, inert material the polymer and indeed unprocessed aggregate material is useful as a mud-pack for skin-care and to carry skin care agents to the skin in mud-pack and peel-off film products;
7. specific application to cosmetics might include lip care. The invention forms a hydramoist complex which has the surprising benefit of being nearly weightless but increasing the lip moisture content. This application could be incorporated in chapped skin lip care, lipsticks, and sun protective products for the lips;
8. face powders for oily skin;
9. as a translucent disguise for wrinkles; and
10. use as a hypoallergenic ingredient in cosmetics and skin care products.

In addition, it is very likely the polymer could be used in certain food applications, namely:
1. this polymer may be especially useful where mixing can be thorough before the acidification/thickening effect is achieved by addition of the polymer to the mixing process. The polymer's effect occurs rapidly after neutralizing;
2. because of its thermal stability this polymer has uses in preparations which "deteriorate at" high temperature treatments;
3. a natural food bulking agent for health food consciousness and first-line medical therapy where bulk agents are indicated; and
4. a natural viscosity-texture modifier for use as fat substitutes.

Other cosmetic applications which might be indicated, include the following:

In the area of therapeutic applications as previously discussed herein it can be used in a wide variety of therapeutic compositions such as:
1. drugs, active chemicals, germicides, perfumes, therapeutic agents, deodorants, etc. can be released in a controlled manner from the gel after the active is incorporated during the setting of the gel by neutralization. The controlled release can be pulsed by the incremental addition of alkali to neutralize the gel;
2. it can be used to maintain a firm gel unit until it is neutralized by, for example, the saliva in human or animal oral environments, thus releasing flavor, fluoride, antibacterial, drug, odor absorber, local anesthetic, etc., into the oral cavity;
3. for controlled release at other sites such as in capsules, tablets, suppositories, and other treatment gels. In some such applications the low residue of solids may be of particular value;
4. it may also be of use where saliva glands are compromised or destroyed, lost, or surgically removed. A gel lozenge or liquid could provide a non-acidic, slow source of saliva substitute. The very slight acidity may stimulate residual saliva glands to aid the lozenge;
5. the same hydrating and protective properties of this substance make it ideal for a bandage. It could be an important addition to the already existing lines of bandages in several ways. It would form a water soluble wash-off Band-Aid. It would be ideal for bandaging massive areas with a minimum of pressure to the damaged skin. Massive bandages incorporating a glycerin solution would significantly hydrate and moisten damaged skin. It has great potential for an actual skin replacement or long lasting occlusive dressing, as is needed for protection of burn patients;
6. the compound was found to be surprisingly useful for medicated lozenges, e.g. cold lozenges, sore throat lozenges, dry throat lozenges, and congestion of nose, throat and lungs due to both seasonal allergies and viral infections;
7. as an oral aid to cure nicotine addiction;
8. a diabetic dietary aid;
9. a glucose regulating aid;
10. the polymer's controlled release mechanism may be utilized for controlling the release of drugs, prodrugs, and glucose in the gastrointestinal tract and other predetermined sites;
11. it may be useful for coating of drugs, especially foods, tablets, and capsules. The fact that it is noncalorific and noncariogenic and a noncarbohydrate makes it the ideal coating for pharmaceutical actives. Diabetics will not have to worry about the sugar content of the traditional sugar and shellac enteric coatings;
12. controlled release of actives such as antiperspirants, deodorants, degreasing, and anti-baldness agents can be facilitated; and
13. it can be used for a gelled alcohol for acne treatment.

The following examples are offered to illustrate but not in any way limit both the cosmetic and therapeutic composition use of the bacterial derived polymer gel compositions.

All the products made in Examples 1 through 2 were found by the users to be long lasting, to provide effective skin moisturization, to be good emollients, to be cosmetically elegant, and to provide excellent skin feel. Moreover, since the products were judged by the users in comparison with other emulsion products utilized by the consumers, those of the invention were substantially preferred. The drug compositions were found to have an excellent epidermal penetration and in comparison with others that did not use the composition of the present invention found to have good drug transfer rate.

EXAMPLE 1

The Use of a Beta,1-3 Polyglucan Homopolymer in Cosmetics

In a series of tests to seek ways of controlling transepidermal water loss (TEWL) it was discovered that a natural microbial polysaccharide polymer which traps 33 times its own weight of water in a non-greasy, non-tacky layer was particularly effective and particularly pleasant to use.

To solutions of 10% glycerol in water, 1%, 2%, 5% and 10% dry weight of the polymer as earlier described in the specification derived from ATCC No. 53703, strain K.U. were added to produce a series of slightly misty, colorless, odorless liquids of neutral pH and viscosity similar to a light hand lotion.

The lotions were applied ad lib to the back of one hand, water alone being applied to the back of the contra-lateral hand. Volunteers were asked to comment on the feel of the water-treated and moisturizer-treated areas at zero, 5, 10, 20, and 30 minutes.

Five out of five volunteers found that the effect of water only had disappeared before 30 minutes. Five out of five found that the moisturizer-treated area felt moisturized for at least 30 minutes and that the treatment was pleasant to apply and non-tacky and non-greasy to touch throughout the trial period. One volunteer detected a diminution of the moisturizing effect at the 30 minutes time interval.

The test demonstrates that microbial Beta,1-3 polyglucan homopolymer polysaccharide derived from ATCC No. 53703, strain K.U. enhanced the moisturizing effect of water without causing the skin feel to deteriorate in any way.

EXAMPLE 2

Use of Polymer Formulations in Pharmaceutical, Therapeutic, Engineering and Food Applications A. Burn Dressing—15% slightly alkaline solution of polymer is poured onto burned areas to provide occlusion, cooling and protective film as it dries out. The protective film will wash off without touching damaged skin, especially if slightly alkaline wash-off solution offered as treatment adjunct.

Controlled release topical ointment/gel:
2-5% polymer
0.025% betamethasone benzoate
0.0% Ethanol
0.1% Methyl paraben
Remainder water B. Drug Coating—15% alkaline solution coated and dried onto tablets of wide range of drugs, to replace sugar coating or other calorific coatings; especially useful for diabetics.

C. Saliva Substitute Lozenge
5-10% polymer
0.2% citric flavor
0.1% ascorbic acid
Preservative
Remainder water D. Medicated Saliva Substitute/Mouthrinse/Lozenges
0.5-10% polymer
0.5% suspension of Nystatin
0.2% flavor
0.1% ascorbic acid
(0.12% Chlorhexidene Di-gluconate) as an alternative to nystatin
2% ethanol
Remainder water E. Therapeutic gel—
(1) Cooling gel for stings, burns, abscesses
20% glycerol
2.5 polymer
0.05% chlorhexidene
Remainder distilled water
Apply liberally in washing mode, then wet loose bandage covering with solution and allow cooling effect of controlled evaporation to soothe inflamed area.

(2) Winter Xerosis treatment
25% glycerol
3% polymer
Preservative
Remainder water
Apply thin film and rub in gently morning and night and after a shower or bath.

F. Food Additive—5% added to oil/water/surfactant prior to emulsification. Yields a firmer, lower calorie butter, fat or margarine substitute. Also lower fat and cholesterol products. Stabilizes emulsions of food and non-food systems.

In other tests it can be 1-10% added as a natural, non-calorific thickener, stabilizer to range of natural and semisynthetic foods such as milk shakes, yogurt, and sauces.

It can therefore be seen that the invention accomplishes at least all of its stated objectives.

What is claimed is:

1. A topical composition for application to skin comprising:
   a topically active agent selected from the group consisting of cosmetics, therapeutics and pharmaceuticals; and
   a small but carrier effective amount of beta 1,3 glucan polysaccharide polymer which is a metabolic product of the gram positive bacteria *Cellulomonas flavigena* or genetic clones thereof.

2. The topical composition of claim 1 wherein the Cellulomonas bacteria is selected from the group consisting of American Type Culture Collection deposit numbers 23199, 482, and 53703.

3. The topical composition of claim 1 wherein the microorganism is *Cellulomonas flavigena*, strain K.U.

4. The topical composition of claim 1 wherein the amount of bacterial polysaccharide polymer gel in said composition is from 0.5% to 10%.

5. The topical composition of claim 4 wherein the amount of bacterial polysaccharide is from 0.5% to 5.0%.

6. A method of delivery of a topically active agent selected from the group consisting of cosmetics, therapeutics and pharmaceuticals, comprising:
   adding a topically active agent to a small but carrier effective amount of beta 1,3 glucan polysaccharide polymer which is a metabolic product of the gram positive bacteria *Cellulomonas flavigena* or genetic clones thereof, to provide a topically active composition; and
   applying said composition to the skin.

* * * * *